United States Patent
Klingenbeck-Regn

(10) Patent No.: US 9,406,134 B2
(45) Date of Patent: Aug. 2, 2016

(54) IMAGE SYSTEM FOR SUPPORTING THE NAVIGATION OF INTERVENTIONAL TOOLS

(75) Inventor: Klaus Klingenbeck-Regn, Nürnberg (DE)

(73) Assignee: SIEMENS HEALTHCARE GMBH, München (DE)

(*) Notice: Subject to any disclaimer, the term of this patent is extended or adjusted under 35 U.S.C. 154(b) by 2122 days.

(21) Appl. No.: 12/077,631

(22) Filed: Mar. 20, 2008

(65) Prior Publication Data

US 2008/0242971 A1    Oct. 2, 2008

(30) Foreign Application Priority Data

Mar. 22, 2007    (DE) .......................... 10 2007 013 807

(51) Int. Cl.
*A61B 6/12*    (2006.01)
*G06T 7/00*    (2006.01)
(Continued)

(52) U.S. Cl.
CPC . *G06T 7/004* (2013.01); *A61B 6/12* (2013.01); *A61B 90/36* (2016.02); *G06T 7/0012* (2013.01);
(Continued)

(58) Field of Classification Search
CPC ........ A61B 6/12; A61B 19/201; A61B 19/52; A61B 10/0233; A61B 19/2203; A61B 2019/501; A61B 2019/5289; A61B 6/03; G06T 7/0012; G06T 7/004; G06T 2207/30052; G06T 2207/10072; G06T 2207/10121; G06T 2207/20221; G06T 2207/30021
USPC ......... 600/407, 424, 411, 427–428, 595, 568, 600/564, 439, 425, 437, 429, 118; 606/130; 382/139; 904/8
See application file for complete search history.

(56) References Cited

U.S. PATENT DOCUMENTS 5,930,329 A * 7/1999 Navab .......................... 378/98.12
6,336,899 B1 * 1/2002 Yamazaki ..................... 600/443
(Continued)

FOREIGN PATENT DOCUMENTS

DE    102004061591 B3    8/2006
DE    102005012698 A1    8/2006

OTHER PUBLICATIONS

Siemens Medical; syngo DynaCT—"Cross-sectional imaging. Setting the trend in intervention", retrieved from Internet on Mar. 3, 2007, http://www.medical.siemens.com/webapp/wcs/stores/servlet/PSGenericDisplay~q_catalogId~e_-3~a_catTree~e_100001~a_langId~e_-3~a_pageId~e_54232~a_storeId~e_10001.htm.
(Continued)

*Primary Examiner* — Long V Le
*Assistant Examiner* — Colin T Sakamoto

(57) ABSTRACT

The invention relates to an image system and a method for supporting the navigation of interventional tools when performing imaging controlled minimally invasive interventions within the body of a patient in a predetermined intervention plane, which serves to improve the precision and reliability of interventional accesses that are required for performing a histological tissue sample removal under CT or MRT based image-oriented monitoring, or in the context of tumor therapy or pain therapy. Directional deviations, away from the intervention plane, of the actual course of an interventional tool from a predeterminable desired course are captured and presented for display by registering the shortened represented total length or a shortened represented partial length of this interventional tool in the 2D projection representation of a fluoroscopic radioscopy recording that was recorded in a 2D projection direction running normally relative to the intervention plane.

13 Claims, 4 Drawing Sheets

(51) Int. Cl.
*A61B 5/055* (2006.01)
*A61B 6/03* (2006.01)
*A61B 10/02* (2006.01)

(52) U.S. Cl.
CPC .. *A61B 5/055* (2013.01); *A61B 6/03* (2013.01); *A61B 10/0233* (2013.01); *A61B 2034/101* (2016.02); *G06T 2207/10072* (2013.01); *G06T 2207/10121* (2013.01); *G06T 2207/20221* (2013.01); *G06T 2207/30021* (2013.01); *G06T 2207/30052* (2013.01)

(56) References Cited

U.S. PATENT DOCUMENTS

| | | | |
|---|---|---|---|
| 6,546,279 B1* | 4/2003 | Bova et al. | 600/429 |
| 2001/0044578 A1* | 11/2001 | Ben-Haim et al. | 600/424 |
| 2003/0097060 A1* | 5/2003 | Yanof et al. | 600/424 |
| 2003/0114862 A1* | 6/2003 | Chu et al. | 606/130 |
| 2003/0135115 A1* | 7/2003 | Burdette et al. | 600/437 |
| 2003/0220531 A1* | 11/2003 | Cortright et al. | 585/733 |
| 2006/0184012 A1 | 8/2006 | Marzendorfer | |
| 2006/0235287 A1* | 10/2006 | Desmedt et al. | 600/407 |
| 2006/0241451 A1* | 10/2006 | Nakaya et al. | 600/443 |
| 2007/0270687 A1* | 11/2007 | Gardi et al. | 600/425 |
| 2008/0171936 A1* | 7/2008 | Homan | A61B 6/4441 600/424 |

OTHER PUBLICATIONS

Siemens AG, Medical Solutions, "Cross-sectional imaging Setting the trend in intervention", syngo DynaCT, Cross-sectional imaging in the angio suite, Flyer_syngo_DynaCT_2D_English.pdf; 2006.

* cited by examiner

IMAGE SYSTEM FOR SUPPORTING THE NAVIGATION OF INTERVENTIONAL TOOLS

CROSS REFERENCE TO RELATED APPLICATIONS

This application claims priority of German application No. 10 2007 013 807.7 filed Mar. 22, 2007, which is incorporated by reference herein in its entirety.

FIELD OF THE INVENTION

The present invention relates to an image acquisition, image processing and image visualization system which can be used in the field of diagnostic and interventional radiology, and an associated method, for supporting the navigation of interventional tools when performing CT-controlled or MRT-controlled minimally invasive interventions at internal organs, tissue regions, lesions or pathological structures within the body of a patient in a predetermined intervention plane, which serves to improve the precision and reliability of interventional accesses that are required e.g. for performing a histological tissue sample removal (biopsy) that is done under CT-based or MRT-based image-oriented monitoring following local anesthetic, or in the context of tumor therapy or pain therapy.

BACKGROUND OF THE INVENTION

In the context of a CT-controlled or MRT-controlled interventional access, for the purpose of supporting and monitoring the navigation of interventional tools that are required for this, 2D projection images, which are usually generated using fluoroscopic imaging in real time, of the anatomical tissue regions to be treated, the medical instruments that are used and the surrounding regions within the body of a patient who is to be treated, are represented on a display screen. A conventional multidirectional C-arm radioscopy system can be used, for example, for monitoring such an interventional access by means of x-ray imaging. Modern C-arm devices allow a rotatory acquisition of 2D projection recordings of tissue regions that are to be depicted, with subsequent 3D reconstruction of the acquired image data which is then visualized in a three-dimensional format. For this purpose, a 3D data record is calculated from the 2D projection recordings of the relevant tissue regions using suitable digital image processing functions. With regard to the image quality and the visualization possibilities, the resulting 3D depictions have CT-like properties.

In the field of interventional rotation angiography, it is appropriate to cite in particular a technology which has been developed by the firm Siemens and has become known under the product designation syngo DynaCT. syngo DynaCT utilizes the recordings of a rotation angiography and generates an angiography CT image (ACT) therefrom. In the case of a C-arm rotation of 220°, the image acquisition typically takes place within approximately 5 to 10 seconds. The recorded volume can then be three-dimensionally reconstructed directly in the angiography room. The application areas of syngo DynaCT range from the representation of hemorrhages or pathologies of the cranial system to the guidance and inspection of punctures and drainage systems. When visualizing tumors and metastases, e.g. in the liver, syngo DynaCT is also used for supporting therapeutic measures relating to e.g. embolization or RF ablation. Since syngo DynaCT already supplies CT-like images during the performance of an interventional access, a patient who is to be treated need no longer be additionally moved into a computer tomograph for the purpose of generating the image data for two-dimensional projection recordings which must then be converted into a volume data record and presented in graphical form for display.

As an alternative to syngo DynaCT, it is also possible to use CT, PET-CT or MRT-based radiological imaging methods, by means of which image data of two-dimensional projection recordings of interesting tissue regions, organs, lesions, anatomical or pathological structures within the body of a patient who is to be treated can be obtained prior to intervention. This image data must then first be converted into a volume data record of a reconstructed 3D view M of the relevant image objects, matched and merged with the image data of a 2D fluoroscopy image F which shows the surrounding tissue regions of these image objects, and graphically visualized together with this, before an interventional access that must be carried out under image-oriented monitoring can take place.

For the purpose of matching the two images M and F, for the data records of an image object BO which is identically represented in the two depictions, wherein said data records might relate to different location-coordinates systems, it is necessary to determine the position offset and angle offset parameters of a two or three-dimensional coordinate transformation which transfers the coordinates of the one data record to the coordinates of the other data record in each case, thereby bringing the two representations of the relevant image object BO into line with each other. In order to optimize the quality of this transfer (i.e. the quality of the image superimposition when merging both data records), an evaluation function (metric) which is defined over a parameter environment is formed and submitted to an optimization criterion that can be expressed by an extremal condition, wherein said optimization criterion can then be used to find the position offset and angle offset parameters for which the two representations of the image object BO are best superimposed. In other words, the evaluation function therefore assumes its optimum for the case that the two data records are correctly registered.

For the purpose of determining the position offset and angle offset parameters, provision is made for specific image features (also referred to as "anatomical landmarks" below) which are contained in the two data records, that must be matched, of the relevant image object BO and can spatially associated with each other. If these landmarks are artificially applied marking objects, the term "extrinsic" registration is used. As part of this activity, an easily detectable system of orientation points is applied to the patient before the image recording. These fixed points can be mathematically brought into a shared context with relative ease subsequently. In most cases, however, the image data is available without artificially added landmarks. In this instance, the case is one of an "intrinsic" registration. The required image features must often be obtained by means of image analysis methods in this case. This takes place either by detecting anatomical landmarks, wherein this can involve e.g. edges or surfaces of bones, internal organs or clearly delimitable tissue regions within the body of the patient, or a segmentation of specific image features which are contained in both data records takes place before the matching. Intrinsic image features are used e.g. in the context of voxel-based matching methods, which have gained considerable significance in the last decade in the course of the research into intensity-based algorithms that are based on an analysis of "mutual information" $I(G_1, G_2)$ as an evaluation criterion for quantifying the quality of a registration. The registration measure given by the following expression $$I(G_1, G_2) = \sum_{G_1, G_2} p(g_1, g_2) \cdot \log_{10} \frac{p(g_1, g_2)}{p(g_1) \cdot p(g_2)} \quad (1)$$

is based on the Kullback-Leiber divergence (KLD) between the associated probability density functions $p_{G1}(g_1)$ and $p_{G2}(g_2)$ of the gray value distributions in the data records $G_1$ and $G_2$ of two images which must be registered together, wherein $g_1$ and $g_2$ designate two discrete random variables for the gray values contained in these two images. In this case, the Kullback-Leiber divergence on the right-hand side of the formula indicates the extent to which the one distribution varies from the other distribution, since it represents a measure for the reciprocal dependency of the two random variables $g_1$ and $g_2$, which measure is maximal in the case of maximal statistical dependency (i.e. in the case of an optimal registration) and minimal in the case of total statistical independence (i.e. in the case of totally incorrect registration). Since only the gray value information of acquired image data is used for determining $I(G_1, G_2)$, no a priori knowledge or image analysis is required for this in principle.

The significant advantage of syngo DynaCT over conventional image acquisition and image registering systems is that visualized syngo DynaCT image data records reproduce current 3D views of image objects to be represented within the body of a patient, wherein these are already related to the location-coordinates system of a 2D fluoroscopy image of the surrounding tissue regions of this image object and are already optimally registered with the 2D fluoroscopy image, such that it is possible to forgo the use of anatomical landmarks for matching three-dimensionally reconstructed views of pre-interventionally acquired image data of the image object with the image data of the 2D fluoroscopy image, and to forgo the use of an intensity-based registration measure for quantifying the quality of this registration.

SUMMARY OF THE INVENTION

The object of the invention is to increase the precision and reliability of CT-controlled or MRT-controlled minimally invasive interventional accesses by improving the accuracy when guiding an interventional tool (e.g. a puncture needle) which is guided under image-oriented monitoring.

This object is achieved according to the invention by the features in the independent patent claims. Advantageous exemplary embodiments which develop the idea of the invention are defined in the dependent claims.

According to a first subject area, the present invention relates to an image acquisition, image processing and image visualization system which can be used in the field of diagnostic and interventional radiology, in particular, for supporting the navigation of interventional tools when performing CT-controlled or MRT-controlled interventions at internal organs, tissue regions, lesions or pathological structures within the body of a patient in a predetermined intervention plane. In this case, the system according to the invention features a navigation aid tool which captures directional deviations, away from the intervention plane, of the actual course of an interventional tool from a predeterminable desired course by registering the shortened represented total length or a shortened represented partial length of said interventional tool in the 2D projection representation of a fluoroscopic radioscopy recording that was recorded in a 2D projection direction running normally relative to the intervention plane, and which effects the display of said deviations either itself or using the functionality of a separate graphics tool.

The image acquisition, image processing and image visualization system according to the invention can additionally comprise an adjustment and control unit which converts the directional deviations of the interventional tool, which are captured by the navigation aid tool, into an actuating variable for triggering an actuator system which compensates for the directional deviations by means of reverse control.

The interventional tool in this case can be e.g. a puncture needle which is used for performing a histological tissue sample removal that is done under CT-based or MRT-based image-oriented monitoring following local anesthetic, or in the context of a tumor therapy or pain therapy. Without restricting the generality, instead of an interventional tool the relevant object can also be an implant, a catheter, the tube of an endoscope or another medical instrument whose guidance direction must be monitored and possibly adjusted during introduction into and navigation within the body of a patient. The actuator system can be e.g. part of a controllable puncture robot which is used for accurate guidance of the puncture needle.

According to a second subject area, the present invention relates to a method for supporting the navigation of interventional tools when performing CT-controlled or MRT-controlled interventions at internal organs, tissue regions, lesions or pathological structures within the body of a patient in a predetermined intervention plane. The inventive method is characterized in that directional deviations, away from the intervention plane, of the actual course of an interventional tool from a predeterminable desired course are captured and presented for display by registering the shortened represented total length or a shortened represented partial length of said interventional tool in the 2D projection representation of a fluoroscopic radioscopy recording that was recorded in a 2D projection direction running normally relative to the intervention plane.

In this case, the captured directional deviations of the interventional tool can be converted into an actuating variable for triggering an actuator system which compensates for the directional deviations by means of reverse control. The interventional tool can again be e.g. a puncture needle which is used for performing a histological tissue sample removal that is done under CT-based or MRT-based image-oriented monitoring following local anesthetic, or in the context of a tumor therapy or pain therapy, and the actuator system can be part of a controllable puncture robot as described above, which is used for accurate guidance of the puncture needle when the needle is fed in.

Following generation of a 3D recording of an image object or target zone to be represented, or following conversion of image data that was acquired prior to intervention into a volume data record of a reconstructed 3D view of this image object or target zone, the method according to the invention initially provides for establishing the spatial coordinates of a puncture target $P_1$ which must be arrived at in the acquired three-dimensional data record and the spatial coordinates of an insertion point $P_0$ with reference to a three-dimensional Cartesian location-coordinates system using a suitably established coordinate origin. The puncture needle is then introduced by a predeterminable length amount in a predeterminable direction into a tissue region which must be examined in the target zone, whereupon according to the invention at least one fluoroscopic 2D radioscopy recording representing the current position of the puncture needle is generated from each of at least two different projection directions. Following detection and identification of the location of the needle tip in the 2D projection recordings of these two projection directions, the location coordinates of the associated spatial point $P_2$ are then calculated in the three-dimensional Cartesian location-coordinates system on the basis of the 2D positions of this spatial point in the two generated 2D fluoroscopy images. This method then provides for the 2D positions of a further suitably established spatial point $P_3$ of the puncture needle to be estimated in the 2D projection recordings of the two projection directions, and the location of this further spatial point to be identified in the two generated 2D projection recordings. The location coordinates of this further spatial point $P_3$ are then calculated accordingly in the three-dimensional Cartesian location-coordinates system on the basis of the estimated 2D positions of the relevant spatial point in the two generated 2D fluoroscopy images. The method therefore ends in that the estimated position of the further spatial point $P_3$ is adjusted by iteratively changing its position until the directions of the 2D projections of a spatial straight line connecting the spatial points $P_2$ and $P_3$ correspond to the projected spatial directions of the puncture needle in the two generated 2D fluoroscopy images to within a predeterminable deviation amount.

The method according to the invention can also provide for the generation of the at least one fluoroscopic 2D radioscopy recording, representing the current position of the puncture needle, from each of the at least two different projection directions to be carried out with the aid of either a C-arm x-ray recording device or with the aid of a biplanar radioscopy system (biplanar system).

In the context of the method according to the invention, provision can additionally be made for detecting two punctual object markings which are applied to the tip or the surface of the puncture needle at the points which are established by the two spatial points $P_2$ and $P_3$.

According to a third subject area, the present invention relates to a method for supporting the navigation of interventional tools when performing CT-controlled or MRT-controlled interventions at a predetermined intervention plane with the aid of a biplanar radioscopy system (biplanar system). The method is characterized in that directional deviations, away from the intervention plane, of the actual course of an interventional tool from a predeterminable desired course are captured and presented for display by registering two angle amounts in the 2D projection representations of two fluoroscopic radioscopy recordings that were recorded in two different projection planes running normally relative to the intervention plane, wherein the two angle amounts are the directional deviations between a desired straight line that is depicted in the relevant projection plane by means of 2D projection of the intervention plane and the projected actual course of the interventional tool in this projection plane.

In this case, the captured directional deviations of the interventional tool can be converted into an actuating variable for triggering an actuator system which compensates for the directional deviations by means of reverse control. The interventional tool can again be e.g. a puncture needle which is used for performing a histological tissue sample removal that is done under CT-based or MRT-based image-oriented monitoring following local anesthetic, or in the context of a tumor therapy or pain therapy, and the actuator system can be part of a controllable puncture robot as described above, which is used for accurate guidance of the puncture needle when the needle is fed in.

Following generation of a fluoroscopic 2D radioscopy recording representing the current position of the puncture needle in a first projection plane running normally relative to the intervention plane, the needle guidance direction in this first projection plane is initially captured in this case. If a directional deviation exceeding a predeterminable angle amount is detected between the actual insertion path of the needle and an ideal insertion path, which is predetermined by the course of a desired straight line that is depicted by 2D projection of the intervention plane in the first projection plane, the needle guidance direction is then adjusted to a value which either is less than a predetermined angle amount or fully compensates for the aforementioned directional deviation in this first projection plane. Following generation of a further fluoroscopic 2D radioscopy recording representing the current position of the puncture needle in a second projection plane running normally relative to the intervention plane, the needle guidance direction in this second projection plane is then initially captured. If a directional deviation exceeding a predeterminable angle amount is detected between the actual insertion path of the needle and an ideal insertion path, which is predetermined by the course of a desired straight line that is depicted by 2D projection of the intervention plane in the second projection plane, the needle guidance direction is adjusted to a value which either is less than a predetermined angle amount or fully compensates for the aforementioned directional deviation in this second projection plane. The above described method steps for capturing and adjusting the needle guidance direction in the two projection planes are then iteratively repeated until the insertion path of the puncture needle corresponds to a desired path which runs in the intervention plane without deviation or to within a predeterminable angle amount.

According to the invention, provision can also be made for the normal vector of this plane instead of the intervention plane to be projected into the second projection plane and, if a directional deviation exceeding a predeterminable angle amount is captured between the actual insertion path of the needle and the ideal insertion path (desired path) that is predetermined by the course of a direction vector which is orthogonal relative to the normal vector, for the navigation of the puncture needle in the intervention plane to be adapted to the direction of this direction vector such that the control deviation in the fluoroscopic 2D radioscopy recording of the second projection plane following adjustment is less than the predetermined angle amount or, in the most favorable case, the insertion path corresponds to the desired path.

BRIEF DESCRIPTION OF THE DRAWINGS

Additional features of the present invention are derived from the dependent claims and from the description of exemplary embodiments which are depicted in the following drawings, in which:

DETAILED DESCRIPTION OF THE INVENTION

In the following sections, the system components of the inventive image acquisition, image processing and image visualization system and the steps of the associated inventive method are described in detail with reference to the appended drawings without restricting the generality using the example of a needle puncture.

Figure 1:
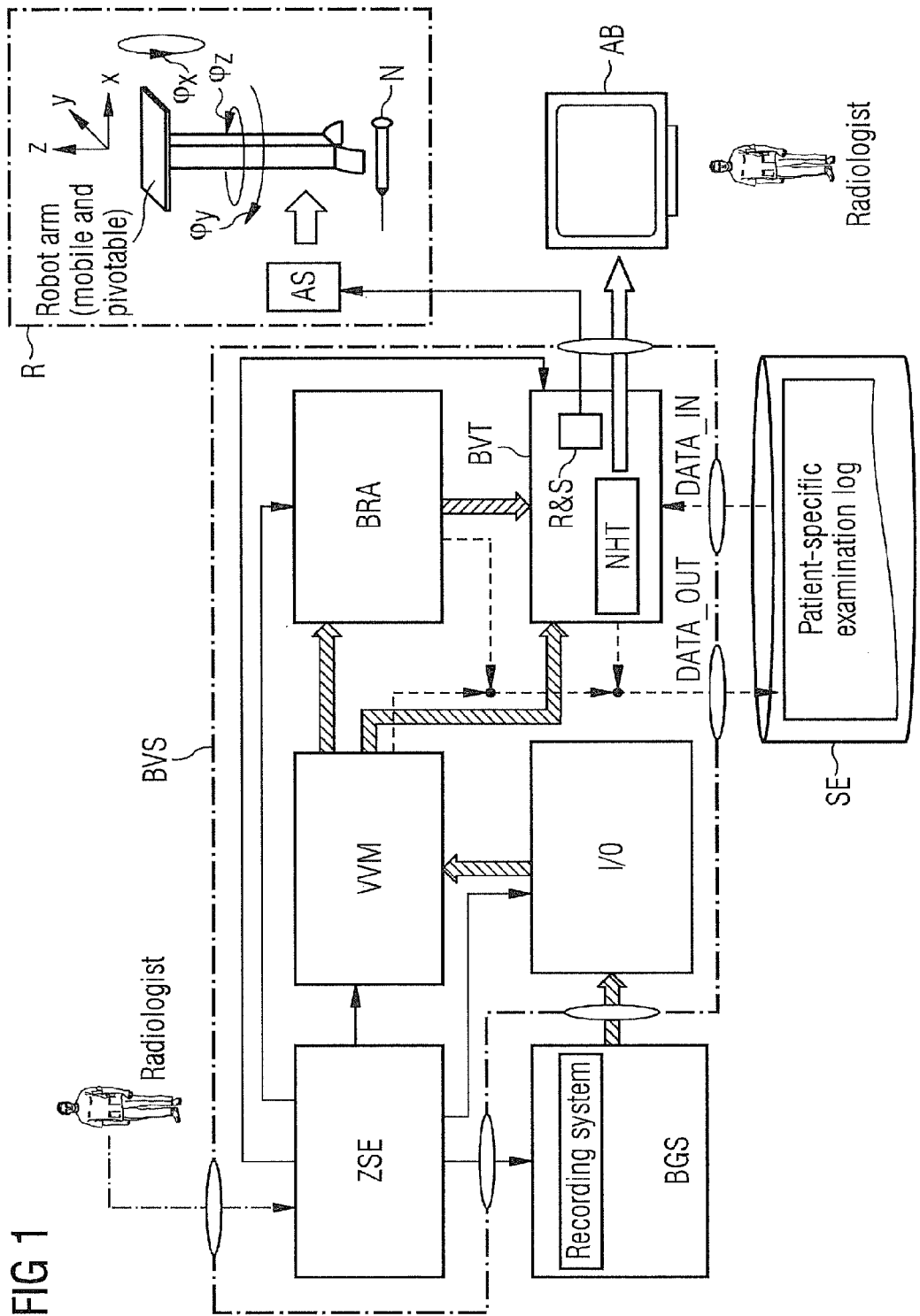
FIG. 1 shows a block schematic diagram of an image acquisition, image processing and image visualization system in accordance with the present invention, which system is used for CT-based or MRT-based image-oriented monitoring of minimally invasive interventions that are performed under local anesthetic at internal organs, tissue regions, lesions or pathological structures of a patient.

FIG. 1 represents a schematic block diagram of an image processing, image visualization and image archiving system in accordance with the present invention, which system allows image data that is generated by an imaging system BGS, said image data relating to internal organs, interesting tissue regions, pathological structures, interventional tools that have been introduced, medical instruments, implants, etc. within the body of a patient who is to be examined, to be captured both in the form of two-dimensional fluoroscopic radioscopy recordings from different projection directions and in the form of three-dimensional reconstructed data records, to be archived, and to be visualized either separately or in the form of matched and merged graphical representations on the display screen AB of a screen terminal. In this case, a conventional CT-device or MRT-device, a C-arm x-ray radiograph device or a biplanar radioscopy system (biplanar system), for example, can be used as an imaging system BGS.

As outlined in FIG. 1, image data that is generated by the imaging system BGS is supplied via an input/output interface I/O to an image processing system BVS. In this case, in addition to a central control entity ZSE which controls the data exchange with the imaging system BGS and the data exchange between the individual system components of the image processing system BVS, the image processing system BVS can comprise inter alia a preprocessing module VVM with a digital filter for noise suppression, contrast enhancement and edge detection. A 3D image rendering application BRA which is integrated in the image processing system BVS is used for generating reconstructed 3D views and for graphical visualization of tissue regions that must be represented. Furthermore, the image processing system BVS also comprises an image visualization tool BVT that is connected on its input side to the data outputs of the preprocessing module VVM and of the 3D image rendering application BRA, and a navigation aid tool NHT, this being integrated in said image visualization tool BVT, which captures and effects the display, on the display screen AB of the screen terminal, of directional deviations, away from an intervention plane E, of the actual course $P_3''P_2''$ of a puncture needle N from a predeterminable desired course $P_3'P_2'$ by registering the shortened represented total length or a shortened represented partial length of said interventional tool in the 2D projection representation 100 of a fluoroscopic radioscopy recording that was recorded in a 2D projection direction $\vec{p}_R$ running normally relative to the intervention plane E, as can be seen on FIGS. 4 and 5. A further 2D projection direction $\vec{p}_R'$, is also visible.

As represented in FIG. 1, the puncture needle N can be guided and controlled either manually by a treatment doctor or by a puncture robot R. According to the invention, an adjustment and control unit R&S which is integrated in the image processing system BVS ensures that the directional deviations of the puncture needle N that are captured by the navigation aid tool NHT are converted into an actuating variable for triggering an actuator system AS which is used for controlling a robot arm and which compensates for the directional deviations by means of reverse control. In this case, the robot arm can ideally be configured such that it is both mobile and pivotable, in order that it can execute movements in up to three translational (x, y, z) and three rotatory degrees of freedom ($\phi_x$, $\phi_y$, $\phi_z$) and hence be able to guide the puncture needle N accurately to a predetermined insertion point and to follow with greater precision a direction of the insertion path, said direction being predetermined by the doctor or by the adjustment and control unit R&S, in the tissue which must be punctured.

Whenever image data is generated by the CT-device or MRT-device and is supplied to the image processing system BVS via an input interface, following completion of the preprocessing and in preparation for a subsequent graphical visualization depending on system configuration, said data can be temporarily or permanently stored in an image data memory of an external memory unit SE under the instruction of the central control entity ZSE, where it is written into a patient-specific examination log of a log file which is held in a memory area of the memory unit SE. In addition to the image data which is acquired in the context of the imaging process, it is also possible for all recording parameters which were manually set by a radiologist carrying out the examination, and all representation and reconstruction parameters that are required for visualizing reconstructed 3D views of specific tissue regions within the body of the patient, to be written to the patient-specific examination log of the externally stored log file in a standardized data format (e.g. in the DICOM format) via a data output interface DATA_OUT of the image processing system BVS. For the purpose of graphical visualization, the stored image data, recording and reconstruction parameters can then be loaded into a local temporary memory (not shown) of the image visualization tool BVT via a data input interface DATA_IN of the image processing system BVS.

It can be seen from FIG. 1 that both the image data from two-dimensional sectional images of tissue regions for examination, said image data having been acquired by means of fluoroscopic imaging and filtered by the preprocessing module VVM, and image data from 3D views of interesting regions from inside the body of the patient, said image data having been reconstructed with the aid of the 3D image rendering application BRA, are supplied to the image visualization tool BVT and then visualized on the display screen AB of the screen terminal in graphical form. For the purpose of archiving, the acquired and reconstructed image data is written via the aforementioned data output interface DATA_OUT of the image processing system BVS (e.g. using the DICOM format) to the patient-specific examination log of the log file which is held in the external memory unit SE, where it is stored in a retrievable and permanent manner.

Figure 2:
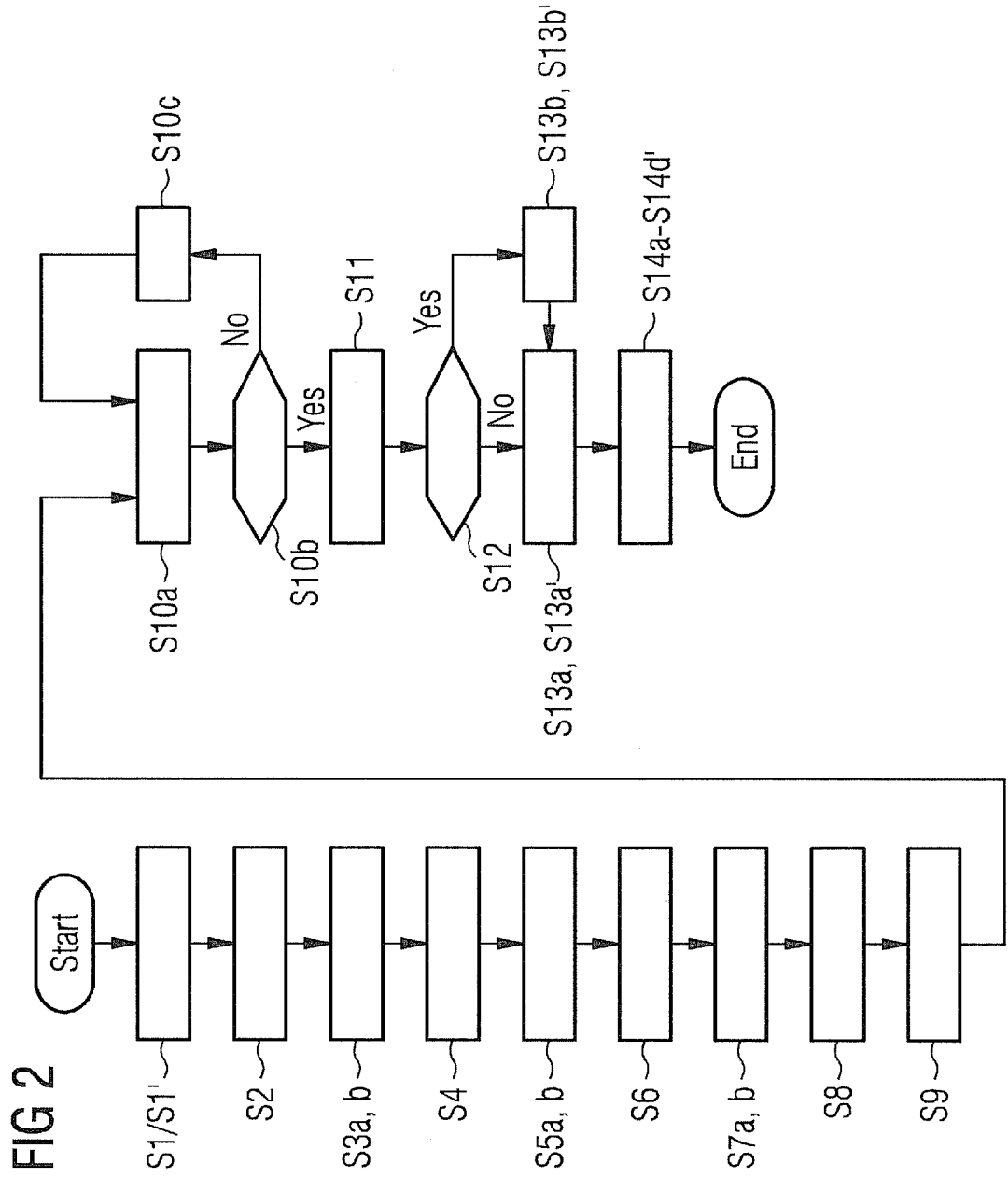
FIGS. 2 and 3 show two different variants of a flow diagram, using the example of a CT-controlled needle puncture, for representing the inventive method for combined registration and visualization of acquired image data which is required in the context of a CT-controlled or MRT-controlled minimally invasive interventional access.

FIG. 2 represents a flow diagram which is used to illustrate the inventive method for CT-based or MRT-based image-oriented monitoring of interventional accesses at internal organs, tissue regions, lesions or pathological structures of a patient, said method being carried out with the aid of the image acquisition, image processing and image visualization system outlined in FIG. 1, with reference to the example of a CT-controlled histological tissue sample removal (biopsy) using a puncture needle N. A conventional multidirectional C-arm x-ray radiograph device, for example, can be used as an imaging system for this. The method starts with the creation (S1) of a 3D recording M of an image object BO that must be represented or of an interesting target zone ZG, e.g. by means of syngo DynaCT. Alternatively, it is also possible to convert (S1') image data which was acquired prior to intervention into a volume data record of a reconstructed 3D view M' of the relevant image object BO or target zone ZG, and if applicable said image data can subsequently be matched, merged and graphically visualized from various viewing angles with the image data of one or more 2D fluoroscopy images that were recorded from different projection directions and show the surrounding tissue regions of this image object or target zone. In a following step (S2), a puncture target $P_1(x_1, y_1, z_1)$ which is described e.g. by three Cartesian location coordinates $x_1$, $y_1$ and $z_1$ (again with the aid of the syngo DynaCT application, for example) is established in the generated 3D data record as an intersection point of three mutually orthogonal sectional planes, these being the projection planes of three 2D projections, that were reconstructed from a volume data record by means of multiplanar reformation, in a three-dimensional cartesian location-coordinates system. The doctor performing the interventional access then establishes a suitable insertion point $P_0(x_0, y_0, z_0)$ (S3a) and introduces the puncture needle N in a specific direction a certain distance into the tissue which is to be examined (S3b). Following thereupon, at least one fluoroscopic 2D radioscopy recording ($F_1$ and $F_2$) representing the current position of the puncture needle N is generated (S4) from each of at least two different angulation directions of the C-arm x-ray radiograph device which is used. In the 2D projection recordings of these two angulation directions, the tip of the puncture needle N is then detected manually or with the aid of a pattern recognition algorithm (S5a) and identified as a point object (S5b), e.g. by means of a colored highlighting of this point object and/or by means of a text label "$P_2$". Since both the geometry and the current position of the detector surface of the C-arm device are known, the cartesian location coordinates $x_2$, $y_2$ and $z_2$ of the associated spatial point $P_2(x_2, y_2, z_2)$ in a three-dimensional cartesian location-coordinates system K can be calculated (S6) from the 2D positions of the needle tip in the two generated 2D fluoroscopy images $F_1$ and $F_2$ using a suitably established coordinate origin O. Following thereupon, the 2D positions of a further suitably determined spatial point $P_3(x_3, y_3, z_3)$ of the puncture needle N are estimated in the 2D projection recordings of the two angulation directions (S7a) and, in a similar manner to step S5, marked in the form of a further point object (S7b), again by means of colored highlighting of this point object and/or by means of a text label "$P_3$", for example. As in step S6, from the 2D positions of this further point object in the two generated 2D fluoroscopy images $F_1$ and $F_2$, the cartesian location coordinates $x_3$, $y_3$ and $z_3$ of the spatial point $P_3(x_3, y_3, z_3)$ are the calculated (S8) in the 3D space which is covered by the cartesian location-coordinates system. Since step S7a is merely based on an estimate, however, it is possible that the spatial point $P_3(x_3, y_3, z_3)$ is actually only a point in the immediate vicinity of the puncture needle N and not a point which is situated on the puncture needle N. For this reason, the location coordinates of the spatial point $P_3(x_3, y_3, z_3)$ are now finely adjusted in a progressive manner with the aid of an iterative method. For this purpose, in a step S9 the two points $P_2(x_2, y_2, z_2)$ and $P_3(x_3, y_3, z_3)$ are connected together by means of a spatial straight line g which is provided by the parameter equation $$g: \vec{X} = \underbrace{\begin{pmatrix} x_2 \\ y_2 \\ z_2 \end{pmatrix}}_{=\overrightarrow{OP_2}} + \lambda_1 \underbrace{\begin{pmatrix} x_3 - x_2 \\ y_3 - y_2 \\ z_3 - z_2 \end{pmatrix}}_{=\overrightarrow{P_2P_3}} (\lambda 1 \in \mathbb{R}) \quad (2)$$

and whose direction vector $\vec{r}_g \equiv \overrightarrow{P_2P_3} = \overrightarrow{OP_3} - \overrightarrow{OP_2}$ forms the spatial direction of a "virtual needle" that corresponds to the spatial direction of the (real) puncture needle N in a first approximation. Following thereupon, the spatial straight line g is projected into the two 2D fluoroscopy images $F_1$ and $F_2$ (S10a). Provided that the directions of both 2D projections of the spatial straight line g correspond to the projected spatial directions of the (real) puncture needle N in the two 2D fluoroscopy images $F_1$ and $F_2$ to within a predetermined acceptable deviation, this being determined by means of a query (S10b), the method can immediately be resumed with the next step (S11). Otherwise, the position of the spatial point $P_3(x_3, y_3, z_3)$ of the virtual needle N is adjusted (S10c) by means of iterative change until the directions of both 2D projections of the spatial straight line g correspond to the projected spatial directions of the real puncture needle N in the two 2D fluoroscopy images $F_1$ and $F_2$ to within a predeterminable deviation amount. In the step S11 following thereupon, the angulation direction of the C-arm is then established such that the projection direction $\vec{p}_R$ of the fluoroscopic radioscopy runs parallel with the normal vector $$\vec{n}_E = \underbrace{\begin{pmatrix} x_2 - x_1 \\ y_2 - y_1 \\ z_2 - z_1 \end{pmatrix}}_{=\overrightarrow{P_1P_2}} \times \underbrace{\begin{pmatrix} x_3 - x_1 \\ y_3 - y_1 \\ z_3 - z_1 \end{pmatrix}}_{=\overrightarrow{P_1P_3}} \quad (3)$$

$$= \begin{vmatrix} \vec{e}_x & \vec{e}_y & \vec{e}_z \\ x_2 - x_1 & y_2 - y_1 & z_2 - z_1 \\ x_3 - x_1 & y_3 - y_1 & z_3 - z_1 \end{vmatrix}$$

$$= \begin{pmatrix} (y_2 - y_1) \cdot (z_3 - z_1) - (z_2 - z_1) \cdot (y_3 - y_1) \\ (z_2 - z_1) \cdot (x_3 - x_1) - (x_2 - x_1) \cdot (z_3 - z_1) \\ (x_2 - x_1) \cdot (y_3 - y_1) - (y_2 - y_1) \cdot (x_3 - x_1) \end{pmatrix}$$

of an intervention plane E which is specified in the parameter form $$E: \vec{X} = \underbrace{\begin{pmatrix} x_1 \\ y_1 \\ z_1 \end{pmatrix}}_{=\overrightarrow{OP_1}} + \mu \underbrace{\begin{pmatrix} x_2 - x_1 \\ y_2 - y_1 \\ z_2 - z_1 \end{pmatrix}}_{=\overrightarrow{P_1P_2}} + \nu \cdot \underbrace{\begin{pmatrix} x_3 - x_1 \\ y_3 - y_1 \\ z_3 - z_1 \end{pmatrix}}_{=\overrightarrow{P_1P_3}} (\mu, \nu \in \mathbb{R}) \quad (4a)$$

or in Hesse's standard form $$E: \vec{n}_{E0} \cdot (\vec{X} - \vec{a}_E) = 0, \quad (4b)$$

where $$\vec{n}_{E0} := \frac{\vec{n}_E}{\|\vec{n}_E\|_2} \text{ und } d := \vec{n}_{E0} \cdot \vec{a}_E > 0, \quad (4c, d)$$

and whose position vector $\vec{a}_E$ is described by the location vector $\overrightarrow{OP_1}$ of the spatial point $P_1(x_1, y_1, z_1)$ in the three-dimensional cartesian coordinate system K and which is covered by two direction vectors $\vec{r}_{E1}$ and $\vec{r}_{E2}$ that are formed by the difference vector $\overrightarrow{P_1P_2}$ between the location vectors $\overrightarrow{OP_1}$ and $\overrightarrow{OP_2}$ of the point pair specified by the two spatial points $P_1(x_1, y_1, z_1)$ and $P_2(x_2, y_2, z_2)$ or by the difference vector $\overrightarrow{P_1P_3}$ between the location vectors $\overrightarrow{OP_1}$ and $\overrightarrow{OP_3}$ of the point pair specified by the two spatial points $P_1(x_1, y_1, z_1)$ and $P_3(x_3, y_3, z_3)$ in this coordinate system K. In this case, the system automatically checks whether a collision of the C-arm is possible (S12). Provided this is not the case, a corresponding angulation direction can be set automatically (S13a) or information is output to the doctor indicating which angulation direction the doctor must set manually (S13a'). If a collision condition exists, the doctor is notified by the system and suggestions are made in terms of the settings that are required in order to ensure that the CT-based examination can be carried out without a collision. This can be achieved, for example, by varying the location coordinates $x_1$, $y_1$ and/or $z_1$ of the puncture target $P_1(x_1, y_1, z_1)$ (S13b). Of course, the new target point must lie within the target zone ZG of interest and must be accepted by the treatment doctor before it can be used by the system. Alternatively, it is also possible to propose a new insertion point $P_0(x_0, y_0, z_0)$ of the puncture needle N (S13b'), which must again be accepted by the treatment doctor first. In the latter case, the steps S3 to S13a/b or S13a'/b' must then be repeated. When the angulation direction of the C-arm is finally adjusted such that the radioscopy takes place parallel with the normal vector $\vec{n}_E$ of the intervention plane E, the triangle $\Delta P_1 P_2 P_3$ is projected into the fluoroscopy image F3 which is generated by this radioscopy. In order to identify the different geometrical elements, i.e. the three spatial points $P_1$, $P_2$ and $P_3$, the triangle $\Delta P_1 P_2 P_3$, the spatial straight line g connecting the two spatial points $P_2$ and $P_3$ and/or the intervention plane E in which the three spatial points $P_1$, $P_2$ and $P_3$ lie, e.g. various colors can be used in the case of a graphical visualization on the display screen of a screen terminal.

Furthermore, it is also possible to draw in a straight line h as specified by the following parameter equation $$h: \vec{X} = \underbrace{\begin{pmatrix} x_3 \\ y_3 \\ z_3 \end{pmatrix}}_{=\overrightarrow{OP_3}} + \lambda_2 \cdot \underbrace{\begin{pmatrix} x_1 - x_3 \\ y_1 - y_3 \\ z_1 - z_3 \end{pmatrix}}_{=\overrightarrow{P_3 P_1}} (\lambda 2 \in \mathbb{R}) \quad (5a)$$

and lying in the intervention plane E, which connects the two spatial points $P_3$ and $P_1$ and hence describes the ideal insertion path of the puncture needle N, e.g. in a green color. In this case, the location coordinates $x_3$, $y_3$ and $z_3$ of the spatial point $P_3$ should be selected favorably close to the insertion point $P_0$. The doctor is then able to withdraw the needle N and immediately bring it to the correct insertion path as specified by position vector $\vec{a}_h = \overrightarrow{OP_3}$ and direction vector $\vec{r}_h = \overrightarrow{P_3 P_1}$ of the straight line h. If the puncture needle N deviates from the ideal insertion path, provision can be made for the target point represented on the screen to flash red, for example.

The fact that the fluoroscopic radioscopy takes place in a spatial direction $\vec{p}_R$ parallel with the normal vector $\vec{n}_E$ of the intervention plane E offers an advantageous monitoring possibility for the needle guidance. If the insertion path leads away from the intervention plane E, the puncture needle N appears more or less shortened in the 2D projection of the fluoroscopy image F3, depending on the angle amount of the relevant directional deviation. In addition to positional deviations, directional deviations of the (real) puncture needle N from the ideal path (shown in green) in the intervention plane E are therefore also directly visible from the fluoroscopic radioscopy image F3 as a result of the projective shortening. This information can then either be visually perceived by the treatment doctor (S14a) and taken into consideration during the needle guidance (S14b) or be captured by the adjustment and control system of a controllable puncture robot R as desired value/actual value deviation (system deviation) (S14a'), analyzed (S14b') and converted into an actuating variable (S14c') which is then used in the context of an automatic needle guidance for directional correction (adjustment) of the insertion path (S14d'). As a result of using such a puncture robot, the accuracy and reproducibility of the needle guidance can be significantly improved in comparison with the needle guidance by a treatment doctor. In this case, the direct exchange of the geometric desired and actual value data of the insertion path between the imaging system of the C-arm device and the puncture robot R allows the intervention method to be largely automated. In this case, however, it is naturally still the responsibility of the treatment doctor to predetermine the location coordinates $x_1$, $y_1$ and $z_1$ of the puncture target $P_1(x_1, y_1, z_1)$ and to select anatomically favorable access paths to the tissue regions which must be punctured in the context of a CT-controlled intervention, such that no bone tissue is in the way and no blood vessels, nerve fibers or internal organs are damaged when the puncture needle N is inserted. For this reason, the inventive method provides for initially executing a test insertion whose insertion path is established by position vector $\vec{a}_g = \overrightarrow{OP_2}$ and direction vector $\vec{r}_g = \overrightarrow{P_2 P_3}$ of the straight line g and therefore by the location coordinates of the two spatial points $P_2$ and $P_3$, i.e. by provisional coordinates which are predetermined by the treatment doctor.

Unlike a method which is known from the prior art, in which the connection straight line $$h': \vec{X} = \underbrace{\begin{pmatrix} x_0 \\ y_0 \\ z_0 \end{pmatrix}}_{=\overrightarrow{OP_0}} + \lambda_3 \cdot \underbrace{\begin{pmatrix} x_1 - x_0 \\ y_1 - y_0 \\ z_1 - z_0 \end{pmatrix}}_{=\overrightarrow{P_0 P_1}} (\lambda 3 \in \mathbb{R}) \quad (5b)$$

between the insertion point $P_0(x_0, y_0, z_0)$ and the puncture target $P_1(x_1, y_1, z_1)$ (subsequently designated "desired straight line") is established as an ideal insertion path, said connection straight line being defined in each case by three cartesian location coordinates in the 3D space that is covered by the cartesian coordinate system K, and in which fluoroscopy images must be recorded from at least two angulation directions of the C-arm, in which the puncture needle N is depicted in different 2D projection representations, in order to compare the current position of the puncture needle N and the direction of the needle feed with the spatial course of the desired straight line h', this being predetermined by its position vector $\vec{a}_{h'} = \overrightarrow{OP_0}$ and direction vector $\vec{r}_{h'} = \overrightarrow{P_0 P_1}$, such an approach is no longer required in the case of the method according to the invention. A further disadvantage of the above described conventional method is that the current insertion point $P_0(x_0, y_0, z_0)$ cannot be represented in the 3D view M' of the target zone ZG, since it cannot be simultaneously represented in both of the at least two different angulation directions, i.e. two-dimensional fluoroscopic radioscopy images $F_1$ and $F_2$ recorded using different projection angles. Both disadvantages are avoided with the aid of the method according to the invention, which provides for a test insertion at a spatial point $P_3(x_3, y_3, z_3)$ that is situated near to the intended insertion point $P_0(x_0, y_0, z_0)$ on the body surface of the patient, since the coordinates of $P_3$ are advantageously selected such that this spatial point is visible in the 2D fluoroscopy images which are generated using both angulation directions and can therefore also be represented in the 3D space. As a result of the inventively predetermined orthogonality between the projection direction $\vec{p}_R$ when performing the fluoroscopic radioscopy and the direction vectors $\vec{r}_{E1}$ and $\vec{r}_{E2}$ of the intervention plane E, the C-arm of the imaging C-arm device can remain in a stationary angulation during the entire CT-controlled intervention.

In order to simplify and make more reliable the detection of the two spatial points $P_2$ and $P_3$ which are situated at suitably established points on the puncture needle N, the invention can further provide for applying two punctual object markings at the relevant points at the tip or on the surface of the puncture needle N. Since the distance between these two object markings is known (i.e. the distance from the point of the puncture needle N which is designated by the spatial point $P_3$ to the needle tip), it can be advantageously used to accurately specify the 3D position of the spatial point $P_3$ if a spatial direction of the puncture needle N is known.

Figure 3:
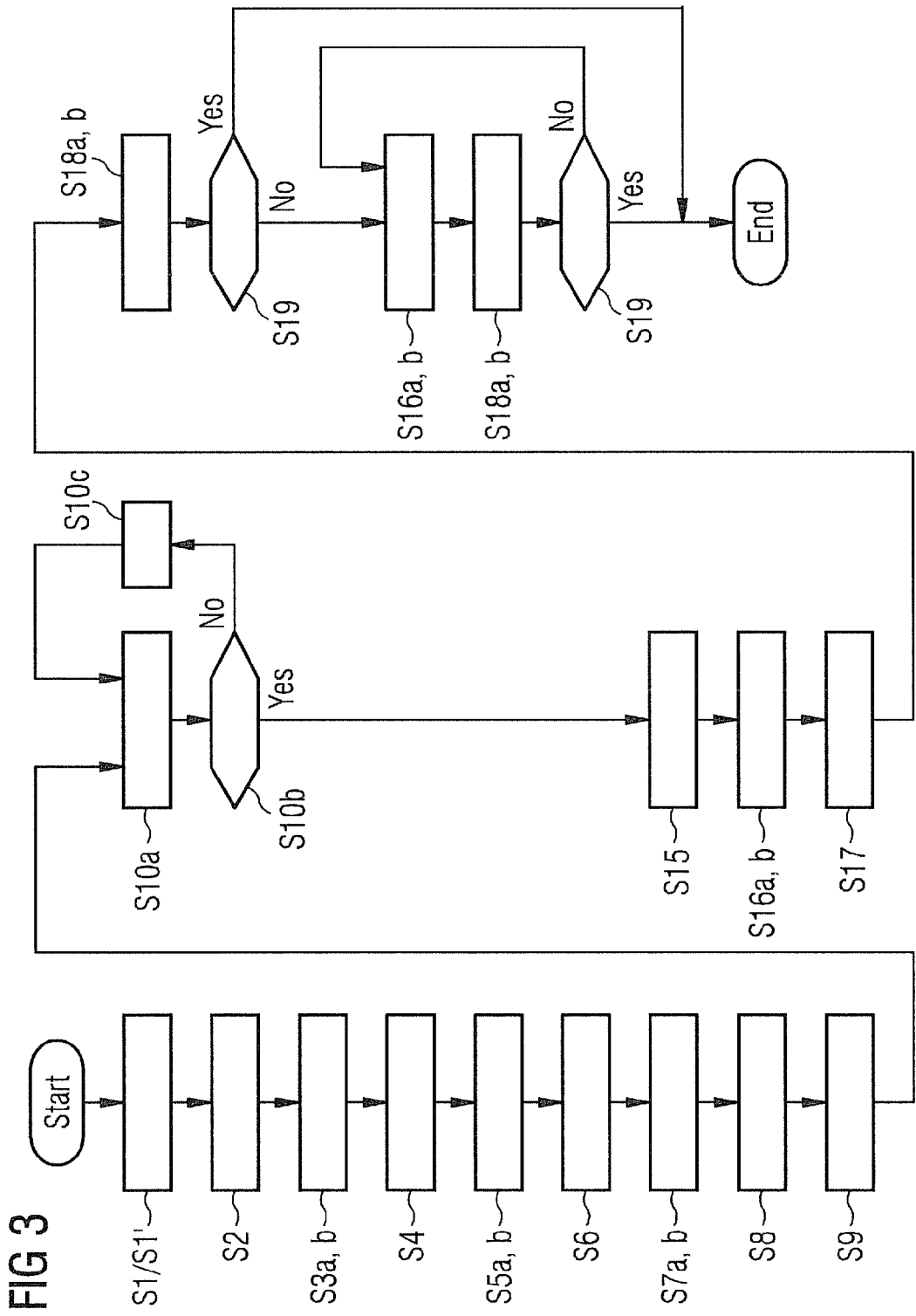
Figure 4:
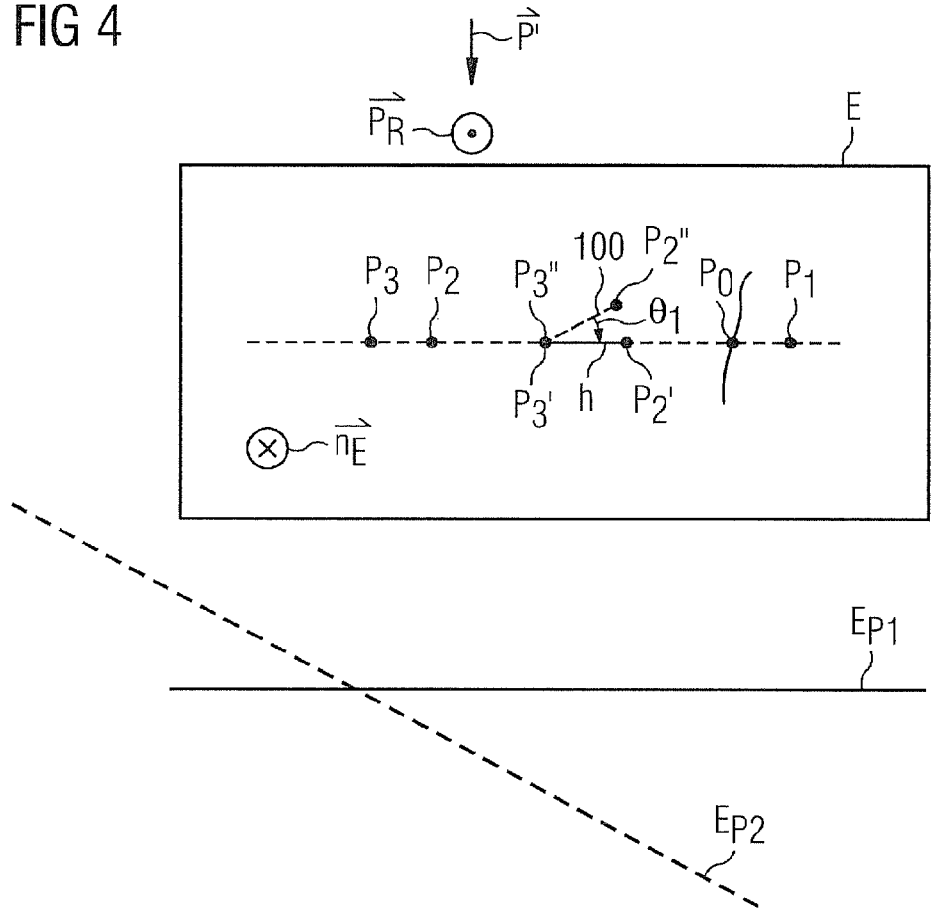
FIGS. 4 and 5 show the intervention plane and projections normal to the intervention plane
Figure 5:
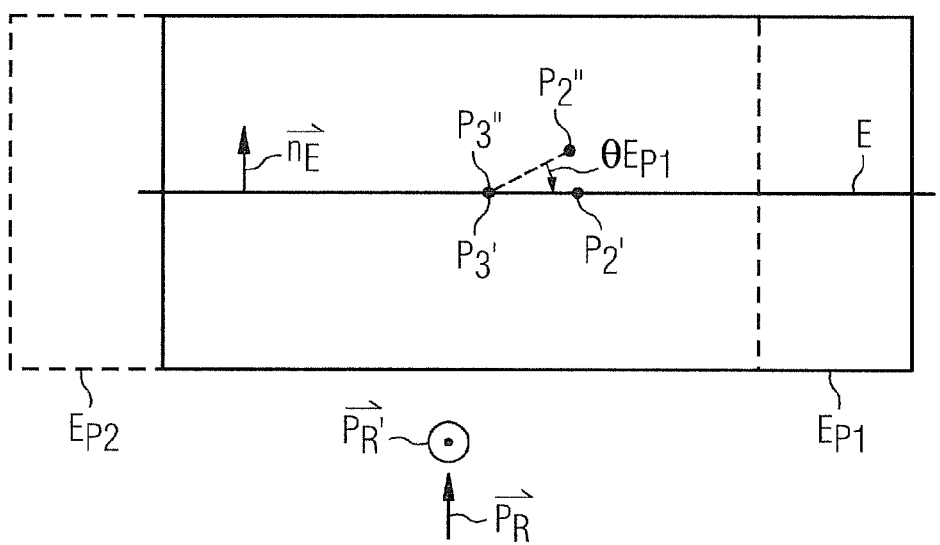

According to a variant of the inventive method, which is carried out with the aid of a biplanar radioscopy system (biplanar system) and represented in FIG. 3, and as also shown in FIGS. 4 and 5, as an alternative to step S11, provision can be made for a projection plane $E_{P1}$ (subsequently also designated "first radioscopy plane") to be angled (S15) such that it runs perpendicular to the intervention plane E. In a similar manner to the method steps S14a and S14b or S14a' to S14d' which are described with reference to the flow diagram outlined in FIG. 2, the navigation of the puncture needle N in the intervention plane E is then captured in this first radioscopy plane $E_{P1}$ (S16a) by means of fluoroscopic radioscopy of the tissue regions to be treated, and adjusted accordingly (S16b) if a directional deviation exceeding a predeterminable angle amount $\Theta E_{P1}$ is detected between the actual insertion path $P_3"P_2"$ of the needle N and the ideal insertion path $P_3'P_2'$ which is predetermined by the spatial straight line h that is represented in green, such that the control deviation in the 2D fluoroscopy image $F_1'$ of this first radioscopy plane $E_{P1}$ following adjustment is less than the predetermined angle amount or, in the most favorable case, the insertion path corresponds to the ideal path represented in green. Following thereupon, the tissue to be treated is radiographed (S17) in a further projection plane $E_{P2}$ (subsequently also designated "second radioscopy plane") which runs perpendicular to the intervention plane E, and need not necessarily run exactly orthogonally relative to the first radioscopy plane $E_{P1}$. In this case, the intervention plane E is depicted as straight line $g_E^{EP2}$ in the 2D projection representation of this second radioscopy plane $E_{P2}$ and is advantageously represented in a color other than the color of the spatial straight line h, e.g. in blue. The straight line $g_E^{EP2}$ therefore reproduces the ideal insertion path of the puncture needle N in this second radioscopy plane $E_{P2}$. Since the depiction geometry of the C-arm device is known, any necessary mathematical corrections can be effected during the projection of the intervention plane E into the second radioscopy plane $E_{P2}$ in order to compensate for any depiction errors. In a similar manner to the above described method steps S16a and S16b, the navigation of the puncture needle N in the intervention plane E is then captured (S18a) in the second radioscopy plane $E_{P2}$, and adjusted accordingly (S18b) if a directional deviation exceeding a predeterminable angle amount $\Theta E_{P2}$ (not shown) is detected between the actual insertion path $P_3"P_2"$ of the needle N and the ideal insertion path $P_3'P_2'$ which is predetermined by the straight line $g_E^{EP2}$ (not shown) that is represented in blue, such that the control deviation in the 2D fluoroscopy image $F_2'$ of this second radioscopy plane $E_{P2}$ following adjustment is less than the predetermined angle amount or, in the most favorable case, the insertion path corresponds to the ideal path represented in blue. If the course of the insertion path in both 2D fluoroscopy images $F_1'$ and $F_2'$ coincides with the green or blue marked ideal path, this being established by the course of one of the two straight lines h or $g_E^{EP2}$ in the relevant 2D projection representation of $F_1'$ or $F_2'$, it is guaranteed that the puncture needle N is moving on the intended insertion path. Otherwise, the method steps S16a, S16b, S18a and S18b are iteratively repeated until the insertion path of the puncture needle corresponds (S19) to a desired path which runs in the intervention plane E without deviation or to within a predeterminable angle amount.

In step S17, instead of the intervention plane E, the normal vector $\vec{n}_E$ of this plane can also be projected into the second radioscopy plane $E_{P2}$ (S17'). In this case, if a directional deviation exceeding a predeterminable angle amount is captured between the actual insertion path of the needle N and the ideal insertion path which is predetermined by the course of a direction vector $\vec{r}_E$ that is orthogonal relative to the normal vector $\vec{n}_E$, the navigation of the puncture needle N in the intervention plane E must be adjusted accordingly, i.e. adapted to the direction of this direction vector $\vec{r}_E$ (S18b'), such that the control deviation in the 2D fluoroscopy image $F_2'$ of this second radioscopy plane $E_{P2}$ following adjustment is less than the predetermined angle amount or, in the most favorable case, the insertion path corresponds to the ideal path represented in blue. In this case, the puncture needle N must therefore be advanced orthogonally relative to the normal vector $\vec{n}_E$ of the intervention plane E.

According to the invention, provision can also be made for the step S4, which is described with reference to the flow diagram represented in FIG. 2 and relates to the generation of at least one fluoroscopic 2D radioscopy recording ($F_1$ and $F_2$) representing the current position of the puncture needle N from each of at least two different angulation directions, to be carried out with the aid of a biplanar system.

The invention claimed is:

1. An image system for supporting a navigation of an interventional tool when performing an imaging controlled invasive intervention within a body of a patient in an intervention plane, comprising:
   a recording system that records a 2D projection recording representing a current position of the interventional tool from two different projection planes running normally to the intervention plane;
   an imaging processing system that processes the 2D projection recording; and
   an input/output interface that receives the recorded 2D projection recording from the recording system and supplies the recorded 2D projection recording to the imaging processing system,
   wherein the imaging processing system is configured to:
      register a shortened length of the interventional tool represented in the 2D projection recording;
      capture a directional deviation of an actual course of the interventional tool from a predetermined desired course that lies within the intervention plane from the registration;
      generate a 3D data record of a target zone of the patient;
      define a spatial coordinate of a puncture target in the 3D data record with respect to a 3D Cartesian coordinate system;

define a spatial coordinate of an insertion point in the 3D Cartesian coordinate system;
identify a position of a tip of the interventional tool in the 2D projection recording;
calculate a location coordinate of the position in the 3D Cartesian coordinate system based on the identified position in the 2D projection recording;
select a further spatial point of the intervention tool in the 3D Cartesian coordinate system;
estimate a position of the further spatial point of the interventional tool in the 2D projection recording;
calculate a 3D location coordinate of the 2D estimated position of the further spatial point in the 3D Cartesian coordinate system;
adjust the further spatial point until a deviation between a direction of a line connecting the identified position of the tip and the estimated position of the further spatial point in the 2D projection recording and a projected direction of the predetermined desired course in the 2D projection recording being within a predetermined deviation value; and
convert the directional deviation of the interventional tool into an actuating variable for triggering an actuator system to compensate the directional deviation by a reverse control,
wherein the intervention plane is defined by the position of the tip of the interventional tool, the further spatial point of the interventional tool, and the puncture target when the intervention tool is properly aligned with a desired path of the intervention tool, and
wherein the image system further comprises a robot that guides the interventional tool introduced from the insertion point to the puncture target based on the actuating variable.

2. The image system as claimed in claim 1, wherein the interventional tool is a puncture needle to remove a histological tissue sample or to perform a tumor or pain therapy.

3. The image system as claimed in claim 1, wherein the shortened length of the interventional tool is a shortened total length or a shortened partial length of the interventional tool.

4. The image system as claimed in claim 1, wherein the intervention is performed under CT or MRT monitoring.

5. A method for supporting a navigation of an interventional tool when performing an imaging controlled invasive intervention within a body of a patient in an intervention plane, comprising:
registering a shortened length of the interventional tool represented in a 2D projection recording recorded in a direction normally to the intervention plane, wherein the shortened length indicates a directional deviation of an actual course of the interventional tool from a predetermined desired course that lies within the intervention plane;
generating a 3D data record of a target zone of the patient;
defining a spatial coordinate of the puncture target in the 3D data record with respect to a 3D Cartesian coordinate system;
defining a spatial coordinate of an insertion point in the 3D Cartesian coordinate system;
introducing the interventional tool from the insertion point into the target zone;
recording the 2D projection recording representing a current position of the interventional tool from two different projection directions;
identifying a position of a tip of the interventional tool in the 2D projection recording;
calculating a location coordinate of the position in the 3D Cartesian coordinate system based on the position in the 2D projection recording;
selecting a further spatial point of the intervention tool in the 3D Cartesian coordinate system;
estimating a position of the further spatial point of the interventional tool in the 2D projection recording;
calculating a 3D location coordinate of the 2D estimated position of the further spatial point in the 3D Cartesian coordinate system; and
adjusting the further spatial point until a deviation between a direction of a line connecting the position of the tip and the estimated position of the further spatial point in the 2D projection recordings and a projected direction of the predetermined desired course in the 2D projection recordings is within a predetermined deviation value,
wherein the intervention plane is defined by a position of a tip of the interventional tool, a further spatial point of the interventional tool, and a puncture target when the intervention tool is properly aligned with a desired path of the intervention tool,
wherein the directional deviation of the interventional tool is converted into an actuating variable for triggering an actuator system to compensate the directional deviation by a reverse control, and
wherein the interventional tool is guided by a robot comprising the actuator system.

6. The method as claimed in claim 5, wherein two markings are arranged to the tip and to the position of the further spatial point of the interventional tool for identifying the position and the further position.

7. The method as claimed in claim 5, wherein the 3D data record is generated by a pre-interventionally acquired image data of the patient.

8. The method as claimed in claim 5, wherein the 2D projection recording is recorded by a C-arm x-ray radiograph device or a biplanar radioscopy system.

9. A method for supporting a navigation of an interventional tool when performing an imaging controlled invasive intervention within a body of a patient in an intervention plane, comprising:
registering an angle amount in a 2D projection recording recorded in a projection plane normally to the intervention plane to capture a directional deviation of an actual course of the interventional tool from a predetermined desired course that lies within the intervention plane;
recording a first 2D projection recording representing a current position of the interventional tool in a first projection plane normally to the intervention plane;
capturing a direction of the interventional tool in the first projection plane;
detecting a first directional deviation;
adjusting the direction of the interventional tool if the first directional deviation exceeding a predetermined angle amount;
recording a second 2D projection recording representing the current position of the interventional tool in a second projection plane normally to the intervention plane;
capturing the direction of the interventional tool in the second projection plane;
detecting a second directional deviation;
adjusting the direction of the interventional tool if the second directional deviation exceeding the predetermined angle amount; and iteratively adjusting the direction of the interventional tool in the first and the second projection plane until the first and the second directional deviation is within the predetermined angle amount, wherein the intervention plane is defined by a position of a tip of the interventional tool, a further spatial point of the interventional tool, and a puncture target when the intervention tool is properly aligned with a desired path of the intervention tool.

10. The method as claimed in claim 9, wherein the angle amount is the directional deviation between a projected line of the desired course of the interventional tool and a projected line of the actual course of the interventional tool in the projection plane.

11. The method as claimed in claim 9, wherein the direction of the interventional tool is adjusted to a value that is less than the predetermined angle amount or to fully compensate the first directional deviation in the first projection plane and the second directional deviation in the second projection plane.

12. The method as claimed in claim 9, wherein a normal vector of the intervention plane is projected into the second projection plane and the predetermined desired course of the interventional tool is determined by a direction vector orthogonally to the normal vector.

13. The method as claimed in claim 12, wherein the direction of the interventional tool is adjusted to a direction of the direction vector if the second directional deviation exceeding the predetermined angle amount.

* * * * *